(12) United States Patent
Avila

(10) Patent No.: US 10,660,600 B2
(45) Date of Patent: May 26, 2020

(54) TABLE TOP IMAGE CALIBRATION PHANTOM

(71) Applicant: ACCUMETRA, LLC, Clifton Park, NY (US)

(72) Inventor: Ricardo S. Avila, Rexford, NY (US)

(73) Assignee: ACCUMETRA, LLC, Clifton Park, NY (US)

(*) Notice: Subject to any disclaimer, the term of this patent is extended or adjusted under 35 U.S.C. 154(b) by 229 days.

(21) Appl. No.: 15/566,177

(22) PCT Filed: Apr. 13, 2016

(86) PCT No.: PCT/US2016/027277
§ 371 (c)(1),
(2) Date: Oct. 12, 2017

(87) PCT Pub. No.: WO2016/168292
PCT Pub. Date: Oct. 20, 2016

(65) Prior Publication Data
US 2018/0035970 A1 Feb. 8, 2018

Related U.S. Application Data

(60) Provisional application No. 62/257,204, filed on Nov. 18, 2015, provisional application No. 62/146,542, filed on Apr. 13, 2015.

(51) Int. Cl.
*A61B 6/00* (2006.01)
*G01T 7/00* (2006.01)
(Continued)

(52) U.S. Cl.
CPC ............. *A61B 6/583* (2013.01); *A61B 5/055* (2013.01); *A61B 6/032* (2013.01); *A61B 6/037* (2013.01);
(Continued)

(58) Field of Classification Search
CPC ......... A61B 6/583; A61B 5/055; A61B 6/032; A61B 6/0407; A61B 8/587; G01T 7/005
(Continued)

(56) References Cited

U.S. PATENT DOCUMENTS 4,985,019 A * 1/1991 Michelson ............... A61B 6/12
128/DIG. 26
5,178,146 A * 1/1993 Giese ..................... G01R 33/58
324/308

(Continued)

OTHER PUBLICATIONS

PCT/US2016/027277, International Search Report and Written Opinion, dated Sep. 26, 2016.

*Primary Examiner* — Taeho Jo
(74) *Attorney, Agent, or Firm* — George A. Leone; Citadel Patent Law

(57) ABSTRACT

A device for measuring image quality properties of an image acquisition device while the subject or object is being scanned contains an embedded grid pattern to measure spatial distortion along the length of the image acquisition table. The device also contains reference materials, which may run along the length of the device, for measuring fundamental imaging properties such as signal strength, noise, and resolution. Automated software can detect the device within an acquisition, measure its properties, and provide data and reports on the quality of the image acquisition.

22 Claims, 7 Drawing Sheets

(51) Int. Cl.
*A61B 8/00* (2006.01)
*A61B 6/03* (2006.01)
*A61B 5/055* (2006.01)
*A61B 6/04* (2006.01)

(52) U.S. Cl.
CPC ............ *A61B 6/0407* (2013.01); *A61B 8/587* (2013.01); *G01T 7/005* (2013.01)

(58) Field of Classification Search
USPC ........................................................ 378/207
See application file for complete search history.

(56) References Cited

U.S. PATENT DOCUMENTS

| | | |
|---|---|---|
| 8,644,906 B2 | 2/2014 | Piferi et al. |
| 2002/0181660 A1* | 12/2002 | Reinstein ............ A61N 5/1048 378/205 |
| 2004/0005035 A1* | 1/2004 | White .................... A61B 6/583 378/207 |
| 2004/0027124 A1* | 2/2004 | Abe ........................ A61B 5/055 324/306 |
| 2008/0093544 A1* | 4/2008 | Wang .................... A61B 6/583 250/252.1 |
| 2009/0315557 A1* | 12/2009 | Slocum, Jr. ............ A61B 6/583 324/308 |
| 2010/0131885 A1* | 5/2010 | Licato .................... A61B 6/482 715/781 |
| 2011/0257919 A1 | 10/2011 | Reiner |
| 2012/0043475 A1* | 2/2012 | Ahn ........................ A61B 6/04 250/453.11 |
| 2012/0238864 A1* | 9/2012 | Piferi .................. G01R 33/285 600/414 |
| 2012/0302863 A1* | 11/2012 | O'Neill .................. A61B 90/39 600/407 |
| 2015/0015922 A1* | 1/2015 | Isaev ...................... H04N 1/047 358/449 |
| 2015/0138349 A1* | 5/2015 | Hebert .................. G01B 11/25 348/136 |
| 2015/0223906 A1* | 8/2015 | O'Neill ................ A61B 6/0492 600/407 |

* cited by examiner

TABLE TOP IMAGE CALIBRATION PHANTOM

CROSS REFERENCE TO RELATED APPLICATIONS

This patent application claims the benefit of U.S. Prov. Ser. No. 62/146,542 filed Mar. 4, 2015 and U.S. Prov. Ser. No. 62/257,204 filed Nov. 18, 2015 both entitled "Table Top Image Calibration Phantom." Both of the above applications are incorporated by reference herein

BACKGROUND

Field of the Invention

The present invention relates to the calibration of imaging systems and, in one aspect, more particularly to a low form factor calibration phantom affixed to the table of an image acquisition scanner that provides calibrated reference geometry in the form of a regularly spaced grid line pattern and reference material samples for image calibration.

Description of the Related Art

Radiological quality assurance phantoms have been developed that evaluate the performance of a scanner with and without a patient or object of study present in the scanner. Calibration phantoms that are designed to be used without an object of study in the scanner cannot directly verify the image quality of actual study scans. They are used to assert that the scanner was operating in a normal range of image quality performance at some time point before the scan took place. In the case of Computed Tomography scanners, calibration with these phantoms is typically performed on a daily basis.

In recent years, phantoms have been developed that are designed to be scanned with the patient that result in scanner reference materials appearing within a patients' scan images. These phantoms have provided reference material samples for Hounsfield Unit (HU) bias correction within quantitative imaging applications where unbiased and precise measurements of x-ray attenuation density is critical. This combined table phantom and measurement software has been implemented for bone density measurements for osteoporosis measurement and monitoring.

More recently table top phantoms have been proposed to capture fundamental properties of an acquisition including resolution, noise, sampling rate, and x-ray attenuation measurement performance for a range of materials. Small calibrated spheres and other objects can be embedded in a calibration phantom that sits on the scanner table and automated software can be designed to measure these image acquisition properties.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

In one embodiment of the present invention a locally thin table top calibration device is affixed to a CT scanner table and provides information on spatial warping and imaging signal properties during patient CT scans.

In another embodiment of the present invention the locally thin table top calibration device is scanned with a patient and an automated software system detects the device, measures the scan properties, and produces data and report on the quality of the image acquired.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1:
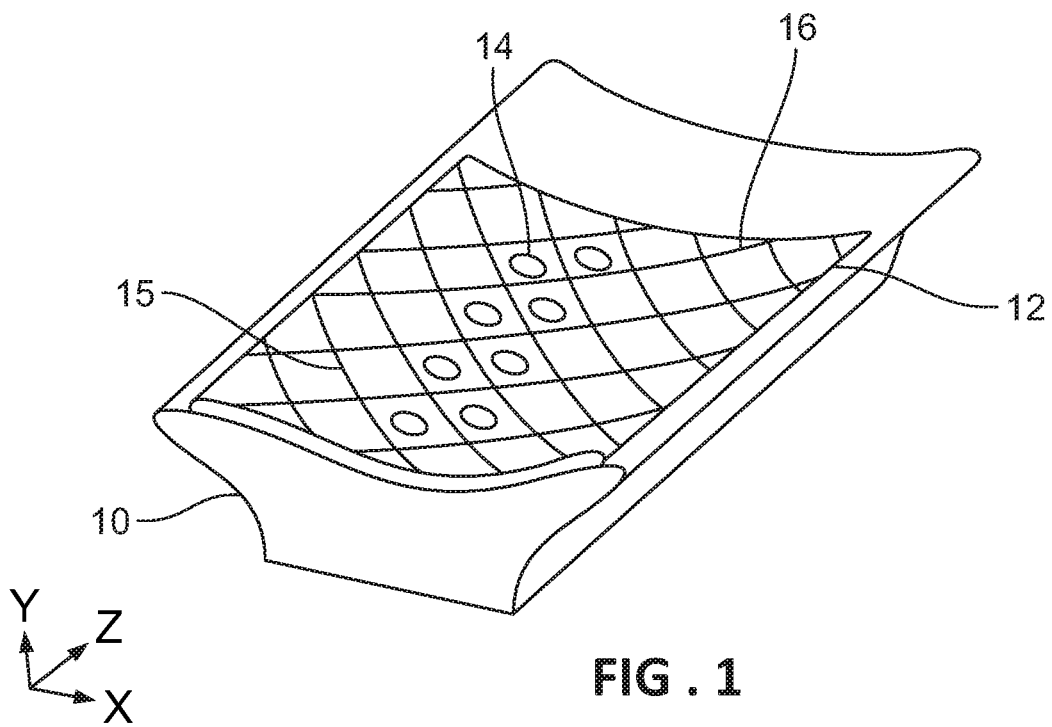
FIG. 1 schematically shows an example of a locally thin, layered, curved image quality calibration device affixed to an acquisition device table.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a calibration device. Several features of methods and systems in accordance with example embodiments are set forth and described in the figures. It will be appreciated that methods and systems in accordance with other example embodiments can include additional procedures or features different than those shown in the figures. Example embodiments are described herein with respect to measuring scanner properties. However, it will be understood that these examples are for the purpose of illustrating the principles, and that the invention is not so limited. Additionally, methods and systems in accordance with several example embodiments may not include all of the features shown in the figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

A limitation of all table top calibration phantom approaches thus far developed is that they do not capture many sources of bias and variation present in modern day medical, security, and industrial scanners, including CT scanners. As a result of this, the ability to measure the performance of a specific scan acquisition is compromised. For example, spatially varying image warping can occur in some CT scanners and acquisition protocols which can significantly degrade the utility of the scan for performing measurements such as volumetric size change measurements. In addition, noise and x-ray attenuation properties can be spatially varying, particularly in CT systems where imaging properties tend to vary radially. Measuring local spatial resolution and x-ray attenuation performance with one set of reference materials near the center of a scanner, as is done with most calibration phantoms, will not fully capture many types of image quality and calibration variation.

Precision manufactured reference objects such as one or more spheres can be used to measure fundamental image properties such as image resolution, x-ray attenuation properties, and noise levels. However, placing precision manufactured and calibrated reference objects at many radial positions within a table top phantom device will result in a prohibitively high cost device. More importantly, if too much high density material is used or these phantom reference objects are placed in linear geometric configurations, the resulting scans can contain significant artifacts. Creating artifacts in the images to be measured is a major problem for phantoms that are scanned simultaneously with patients. The materials and geometry must be designed such that artifacts are minimized.

Figure 2:
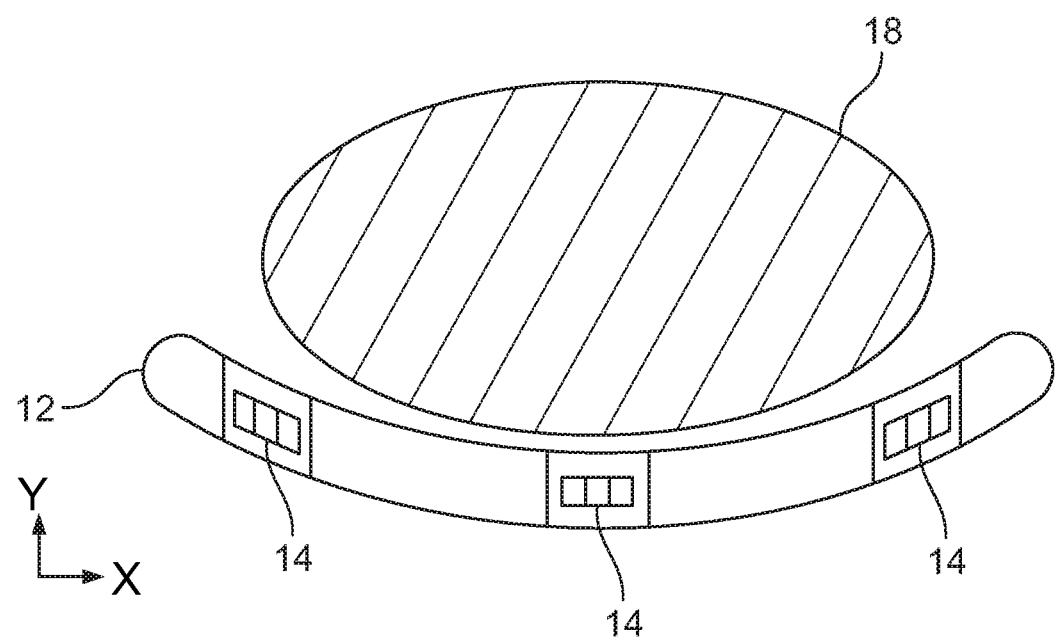
FIG. 2 schematically shows an axial cross section of an object or subject on top of a curved image quality calibration device which is all on top of an image acquisition device table (as shown in FIG. 1).

The present invention uses scanner-aligned cylinders of reference materials that when analyzed with software algorithms result in fundamental image acquisition properties such as the 3D PSF (point spread function), x-ray attenuation, noise and other signal properties of the image. The use of a cylinder or disk shaped geometry, as shown in FIG. 2, exploits the radial symmetry of a CT scan reconstruction. Specifically, since the X & Y resolution of a CT scanner are typically identical and Z resolution is different, it is sufficient to measure just the X & Z resolution to estimate the 3D PSF.

Using a cylinder or disk shaped reference object is also much easier and less costly to manufacture than embedding spherical objects into a calibration phantom, particularly when material homogeneity and precise dimensional tolerances are needed. In fact, most precision manufactured plastic spheres (e.g. Teflon® and Delrin® plastic spheres) are made from extruded rod to arrive at better material homogeneity properties (e.g. without air voids). Disk shaped reference objects also have the potential to utilize the least amount of phantom material, leading to calibration devices that result in lower amounts of phantom generated image artifacts. This is particularly important when deployed for clinical studies involving precise measurements with little tolerance for increased image noise and other artifacts, such as is the case in CT perfusion studies.

Another major source of CT image variation that can impact quantitative measurements is spatial warping, which is particularly associated with helical CT scanning modes. To measure spatial warping, it is highly advantageous to construct a calibration phantom that contains a regular geometric pattern of material and analyze the pattern in the acquired image for spatial deformations. This technique has been successfully developed and deployed using a 3D grid of spheres in the MRI setting. However, as mentioned earlier, a regular grid on a plane of material can cause large CT artifacts and shadows that will obscure and deform the needed reference geometry.

Referring now to FIG. 1, a low form factor diamond shaped grid 16 is placed inside a curved table top phantom 12, which sits on top of a curved table 10 with the same curvature, thereby avoiding opportunities for the phantom grid geometry to form attenuation artifacts and streaks in the resulting images. A diamond pattern 15 is advantageous since there is little opportunity for material to align along the path of x-rays as they travel from an x-ray source to a detector, typically in a fan or cone geometry. Reference object materials 14 are placed at the center and at one or both sides of the calibration device 12. The reference object materials 14 are oriented with the coordinate system of the image acquisition system and are shown here to run down the center of the calibration device 12 as well as down both sides. Each reference object contains an internal material to be measured and a background homogeneous material surrounding the internal material.

This type of table top phantom will need to be affixed to the CT table to maintain high levels of alignment with the scanners coordinate system and acquisition geometry. It is particularly important that the device moves identical to the scanner table during the scan acquisition. Plastic fixtures including the use of snaps, adhesives, and/or a hook and loop fasteners, such as Velcro® fasteners for example, can be added to the CT table to ensure that the CT table top phantom remains in the desired position.

In one embodiment a curved table top phantom consists of high density polystyrene and air to create a high contrast, but low CT density, it has a diamond shaped grid that runs along a substantial length of the CT table. The curved 2D plastic and air grid within such a phantom has diamond shaped air pockets, some of which can be filled with scanner coordinate system aligned and homogeneous reference materials using cylindrical shapes. At a minimum, a set of reference material cylinders running down the center of the table top phantom and along an outer table edge would allow attenuation analysis to look for and characterize radial variation effects. The reference disks 14 should be constructed with a homogeneous internal reference material and a uniform outer material such as urethane. The uniform outer material is used both to protect the integrity of the reference sample and to provide a homogeneous material with which to observe edge effects or partial volume artifact for resolution and other measurements. The size of these disks should be constructed such that they are sufficiently far enough away from the plastic grid pattern so as not to impact the reconstructed densities of the grid. If the reference material is to be used for measuring resolution, as is typically done with Teflon® or other high density materials, the amount of outer material encasing the reference sample must be sufficient to obtain a full transition from reference material signal intensities to outer material intensities. For current CT scanners and protocols this is around 6 mm of outer material.

Figure 3:
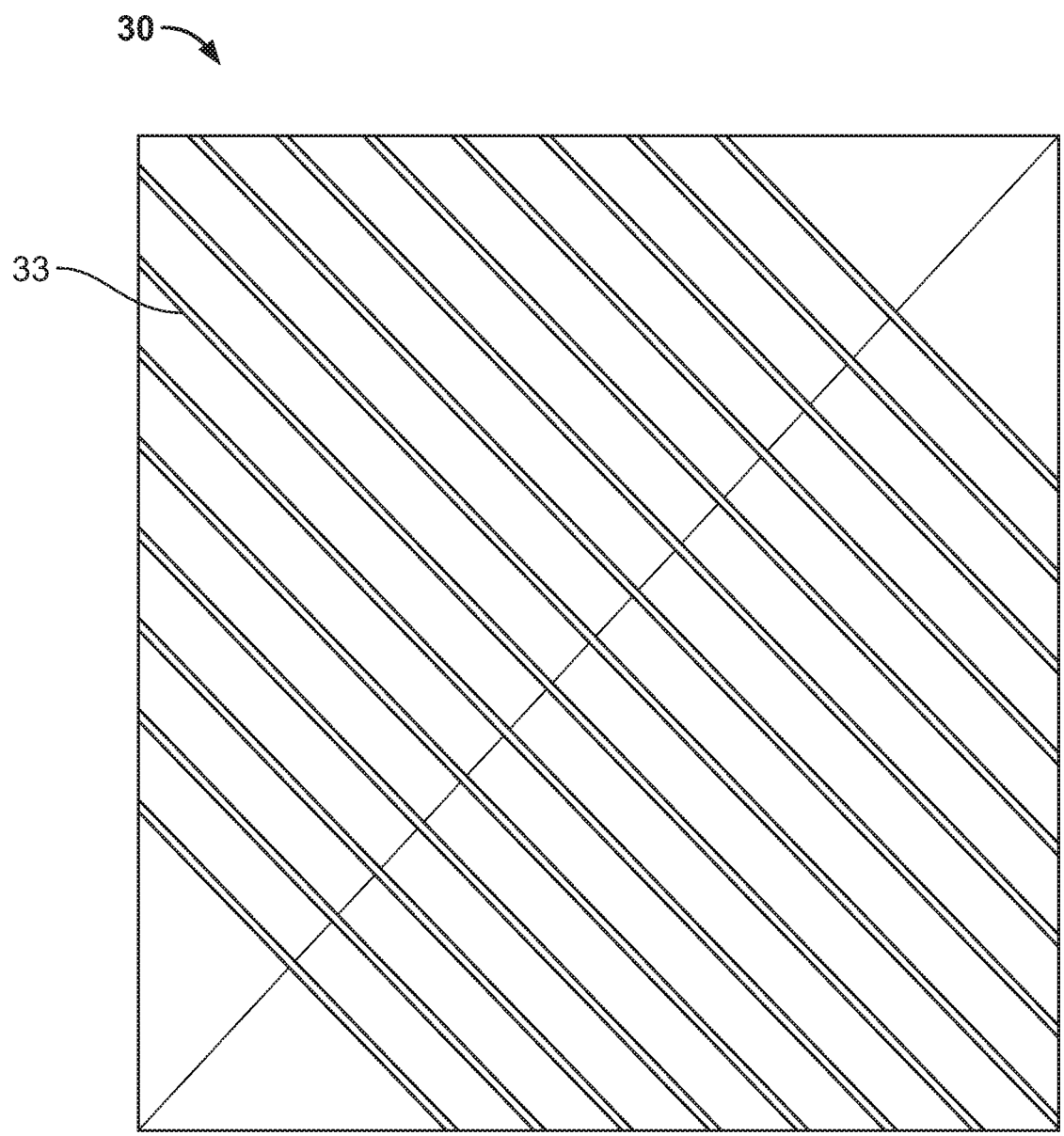
FIG. 3 shows an example of a plastic sheet having a regular pattern of diagonal lines oriented along a first oblique angle.

Referring now to FIG. 3, an example of a plastic sheet 30 having a pattern of diagonal strips 33 oriented along a first oblique angle is shown. The table top phantom may advantageously consist of two such plastic sheets 30A, 30B (as best shown in FIG. 4A) placed one on top of the other with the stripping of one facing and contacting the stripping of the other to form a diamond pattern. In one example the sheets may be made of 1.5 mm thick plastic (e.g. high density polystyrene) each with regularly spaced diagonal strips that are 4 mm wide and 1.5 mm thick and with a 50 mm spacing interval. The diagonal strips may be angled at about 45 degrees.

Figure 4:
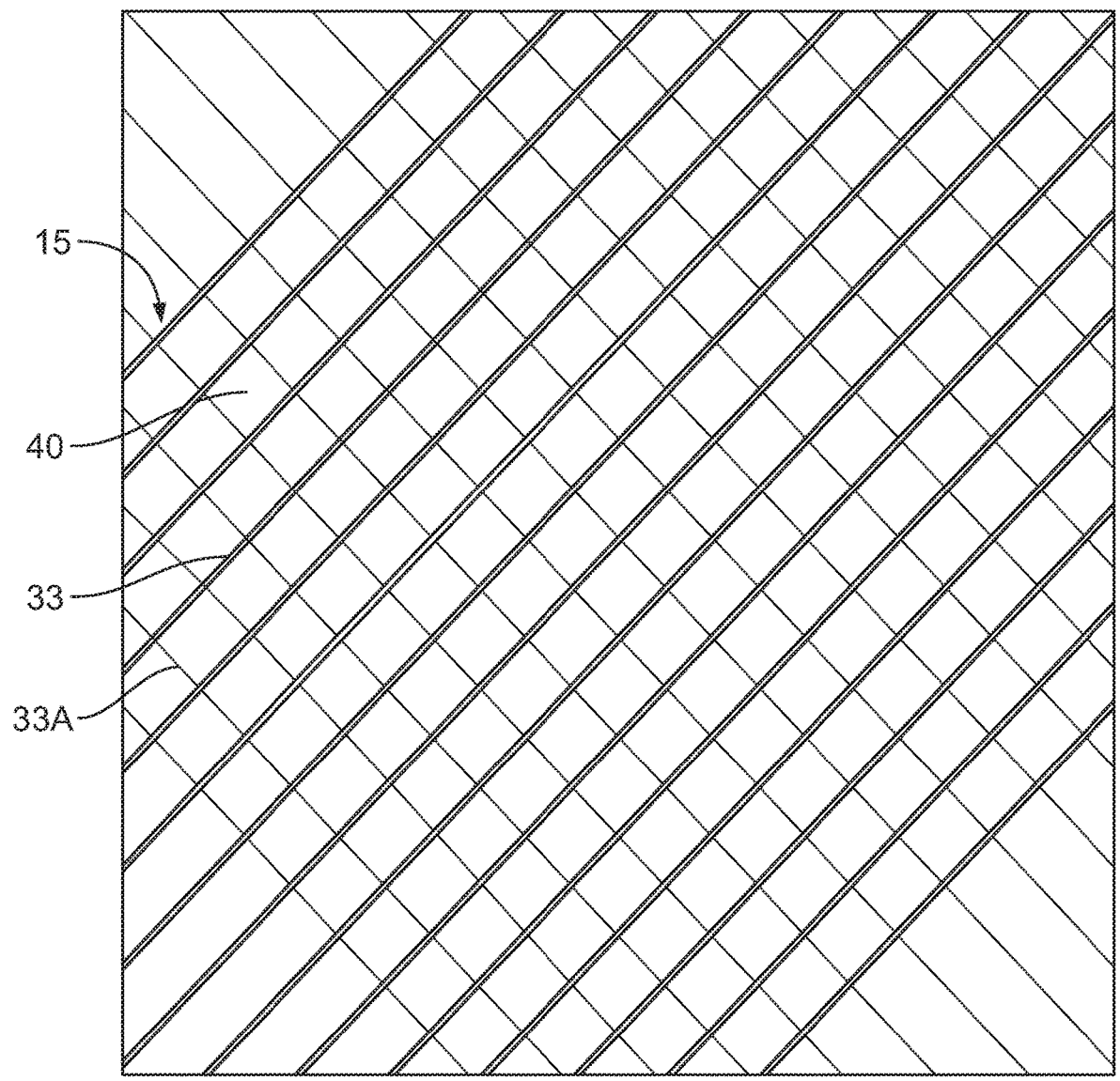
FIG. 4 schematically shows an example of a curved image quality calibration device with a simulated diamond pattern.
Figure 4A:
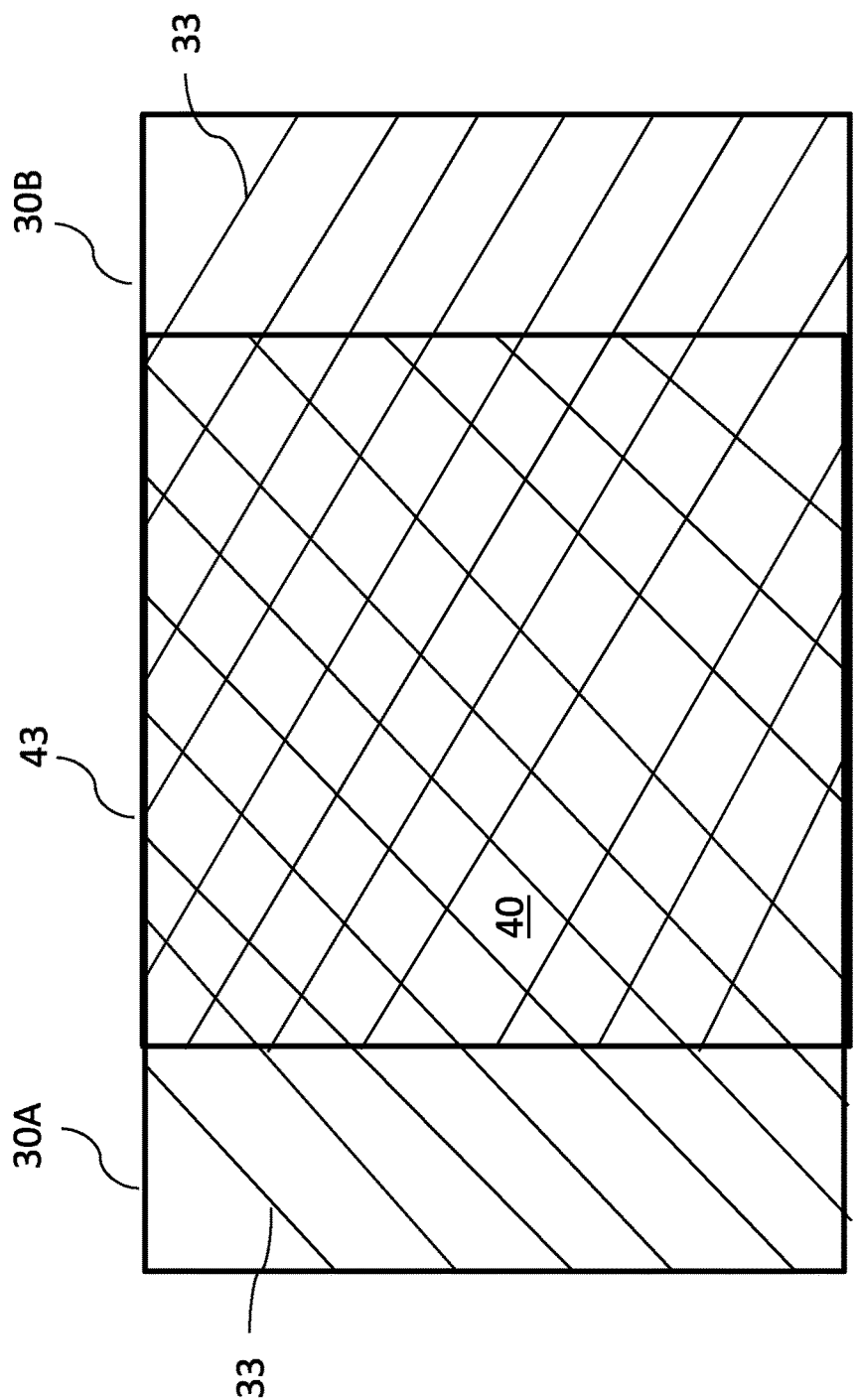
FIG. 4A schematically illustrates formation of a simulated diamond pattern by overlapping diagonally patterned sheets at different orientations.

Referring now to FIG. 4, an example of a curved image quality calibration device with a simulated diamond pattern is schematically shown. The diagonal strips 33 have been augmented with a penciled in set of perpendicular lines 33A to illustrate the final diagonal pattern that results when the two sheets are affixed together. In an actualized embodiment, the diamond pattern 15 will result with diamond shaped air voids 40 available for placing material reference disks. Affixing the two sheets of curved material with regularly spaced strips has the potential to result in a low cost manufacturing process.

Referring now to FIG. 4A formation of a simulated diamond pattern by overlapping diagonally patterned sheets at different orientations is schematically illustrated. A first plastic sheet 30A is overlapped with a second plastic sheet 30B. Each of the plastic sheets include diagonal strips 33 oriented along a preselected axis. The first and second plastic sheets may be identical, for example, and the sheets are rotated 90 degrees with respect to one another such that the diagonal strips 33 form a diamond pattern 15 when the sheets are rotated and overlap with each other. Here, the overlapping area is 43 with air voids 40.

However, in another preferred embodiment the table top phantom containing a diamond grid pattern is constructed as one contiguous grid of plastic material with fittings for disk or sphere shaped reference materials, which can be easier and less costly to obtain and work with. In another preferred embodiment the table top calibration device contains port holes for access to the reference object materials, which can be removed or replaced.

Another optional component of the system is automated analysis software. Automated analysis software can be constructed that detects and measures the table top phantom producing a report that describes the fundamental characteristics of an individual CT acquisition. The automated software can further alert the institution performing the scan of any issues identified when the scan was analyzed.

Figure 5:
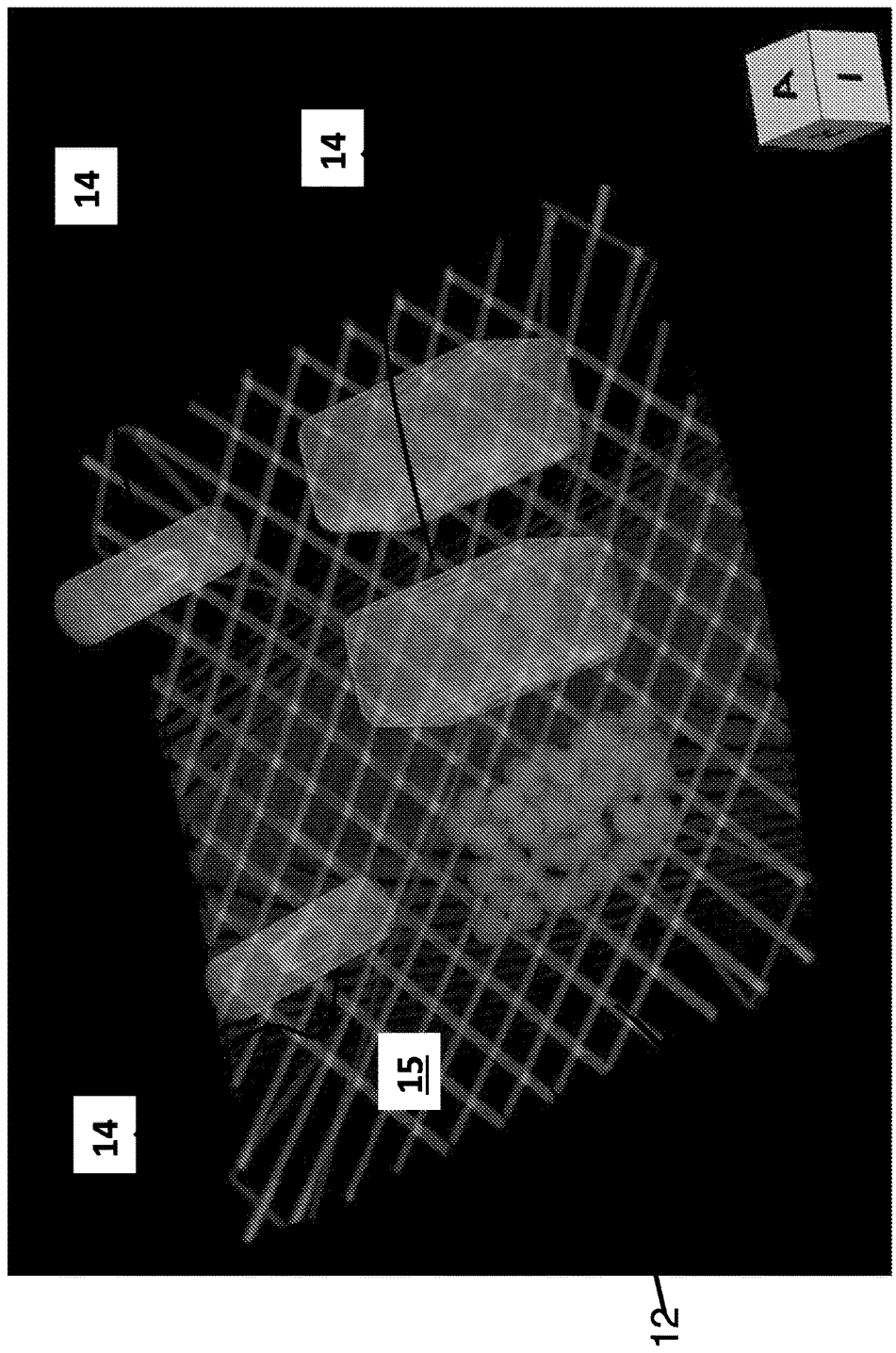
FIG. 5 shows a CT scan of reference material objects on a curved image quality calibration device having a diamond pattern.

Referring now to FIG. 5, a 3D CT scan of reference material objects on a diamond pattern calibration device is shown. A plurality of different reference objects 14 have been scanned on a curved, diamond pattern calibration device 12 as disclosed herein. Once having the scan, the properties of the imaging device can be precisely measured since the dimensions of the reference objects 14 are known.

Figure 6A:
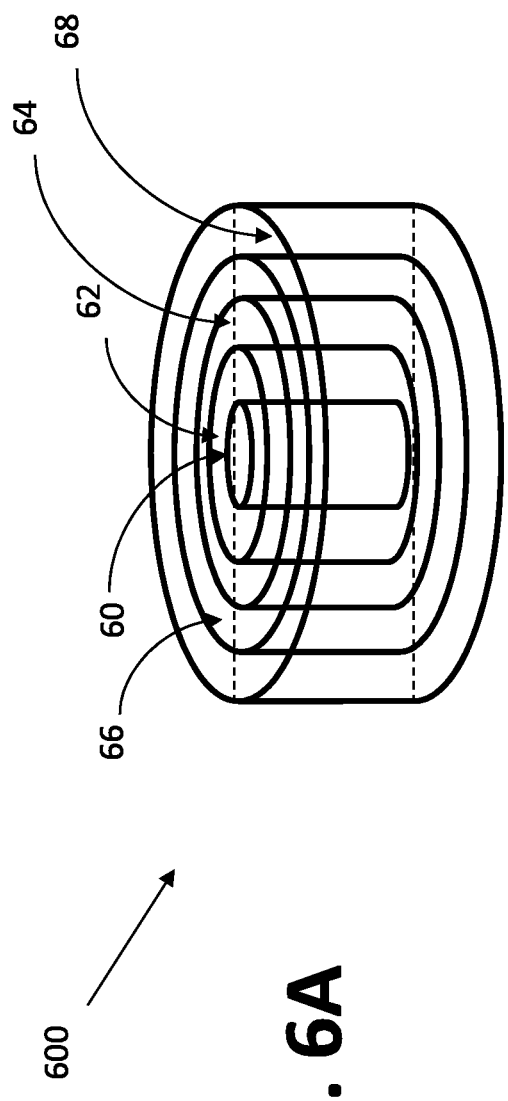
FIG. 6A schematically shows an example of a CT disk phantom comprising multiple precision made concentric rings of different density material.

Referring now to FIG. 6A, an example of a CT disk phantom comprising multiple precision made concentric rings of different density material is schematically shown. A CT disk phantom 600 includes an inner cylinder 60 of air material surrounded by a second cylinder 62 of a high density material, as for example, Teflon® brand Polytetrafluoroethylene (PTFE) or the like. The inner cylinder 60 and second cylinder 62 are concentrically surrounded by a third cylinder 64 of another material, as for example, Delrin® brand Polyoxymethylene (POM), or the like. An optional fourth cylinder 66 concentrically surrounds the inner cylinder 60, the second cylinder 62 and the third cylinder 64. The fourth cylinder may be made of low-density polyethylene (LDPE) plastic or the like, for example. The entire CT disk may be encased in a urethane material 68 except for the inner hole/air material 60. That is, the second through fourth cylinders may be encased in urethane, where the urethane case includes openings on the top and bottom of the CT disk so that the inner cylinder 60 and the inner surface of the second cylinder surrounding the inner cylinder are not covered. The resulting CT disk is an extremely compact shape that has advantages in construction cost and manufacture due to the concentric disk shapes. Due to the compactness only a very small amount of material is needed to make the CT disk. The compact disk keeps artifacts low, particularly when the disk or disks are placed within the aforedescribed table phantom. The distinct concentric disk shapes and materials can easily be automatically detected and measured. Further the ordering of the materials can be varied and switched, or all of the discs and the central air hole can be encased in urethane.

Figure 6B:
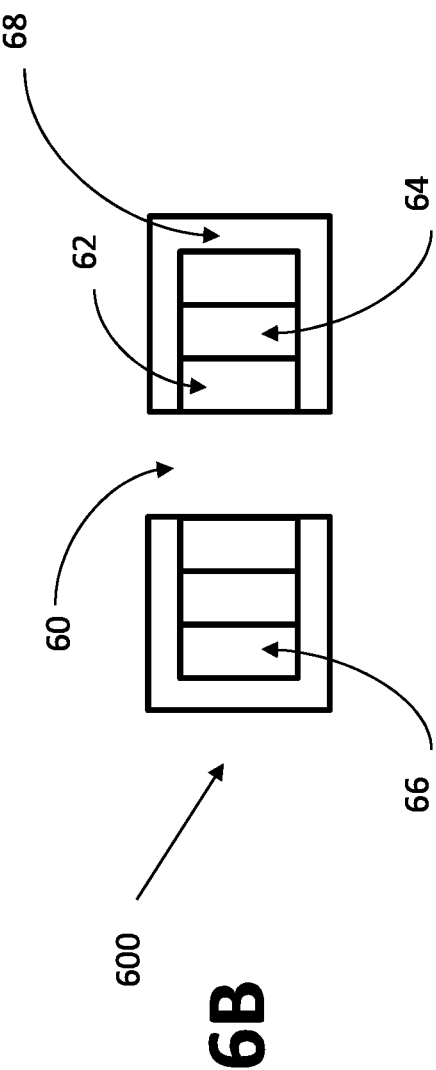
FIG. 6B schematically shows a cross-section view of a CT disk.

Referring now briefly to FIG. 6B, a cross-section view of a CT disk is schematically shown. Here the ordering of the materials comprising the inner cylinder 60, second cylinder 62, third cylinder 64 and fourth cylinder 66 is further illustrated. The urethane casing 68 surrounds the second through fourth cylinders leaving the inner cylinder 60 open and uncovered through the center of the disk.

Figure 7:
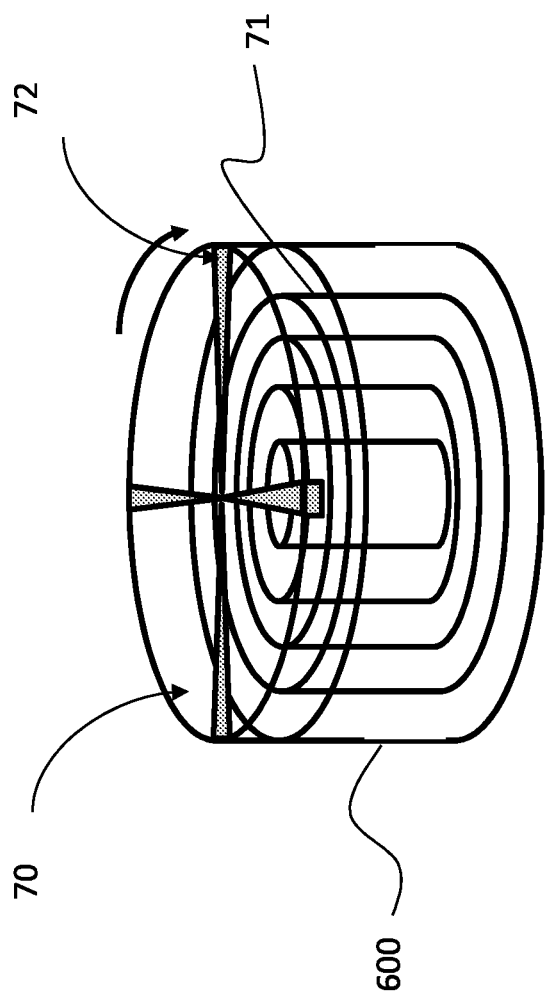
FIG. 7 schematically shows an example of a CT disk phantom with a rotating radial pattern.

Referring now to FIG. 7, an example of a CT disk phantom with a rotating radial pattern is schematically shown. A radial pattern 72 is affixedly centered on the top face 71 of a CT disk 600. A clock 70 is coupled to rotate the top face. The clock may be, for example, a precision wound plastic clock that can uniformly rotate the top face for a few minutes. A resulting rotating pattern can then be used to measure the temporal resolution of a selected scanner. Note that none of the components should contain any metal or very high density materials since such materials would create artifacts in CT. In operation, the clock can be non-metal spring wound (e.g. fiberglass, plastic, or other materials) and cause the CT disk to spin while operating the scanner to obtain scanning images.

An entire disc or group of discs can be CT scanned independently or embedded within a CT table phantom and scanned. The resulting scanned images can then be analyzed to obtain estimates of resolution, x-ray attenuation properties, noise, spatial warping, edge enhancement, and other image quality characteristics.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A phantom device for measuring image quality properties of an image acquisition device while an object or patient is being scanned, comprising:

a locally thin layered substrate adapted to match and be affixed to a curved scanner table top with the same curvature;

wherein the layered substrate has a pattern adapted to indicate position and distortion along the surface of the curved scanner table top;

wherein the layered substrate includes air pockets; and at least one scanner-aligned material reference object embedded within the air pockets of the grid pattern to provide a reference for measuring resolution, noise, and signal response properties.

2. The device of claim 1 wherein the grid pattern comprises a diamond shaped grid pattern.

3. The device of claim 2 where the grid pattern comprises at least two overlapping sheets of material with opposing parallel lines that are regularly spaced.

4. The device of claim 1 wherein the at least one material reference object is placed in air pockets of the grid pattern along the length of the device and running down the length of the scanner's table at the center and along at least one side.

5. The device of claim 1 wherein the at least one material reference object is spherical or cylindrical in shape and oriented with the scanner coordinate system.

6. The device of claim 5 wherein the at least one material reference object comprises an internal material and a different background material.

7. The device of claim 1 wherein the device further comprises fastening elements that allow it to be physically affixed to the scanner table.

8. The device of claim 1 wherein the device further comprises a plurality of ports located to access the material reference objects.

9. The device of claim 1 wherein the device materials are adapted for measuring image quality of CT, XR, PET/CT, NM, MRI, or Ultrasound scans.

10. The device of claim 1 wherein the device materials are adapted for CT multi-energy scanning, including iodine and calcium.

11. In an automated phantom analysis system that can detect and measure the image quality properties of a locally thin image quality measurement device, the improvement comprising:

a phantom device for measuring image quality properties of an image acquisition device while an object or patient is being scanned, the phantom device including a locally thin layered substrate adapted to match and be affixed to a curved scanner table top with the same curvature, wherein the layered substrate has a grid pattern adapted to indicate position and distortion along the surface of the curved scanner table top wherein the layered substrate includes air pockets, and at least one scanner-aligned material reference object embedded within the air pockets of the grid pattern to provide a reference for measuring resolution, noise, and signal response properties.

12. A method for measuring image quality properties of an image acquisition device while an object or patient is being scanned, comprising:

forming a locally thin layered substrate with a regular grid pattern having a plurality of air pockets, the substrate adapted to indicate position and distortion along a curved surface of a curved scanner table top;

matching and affixing the locally thin layered substrate to the scanner table top curved;

embedding at least one scanner-aligned material reference object within the air pockets of the measuring resolution, noise, and signal response properties.

13. The method of claim 12 wherein forming a locally thin layered substrate with a regular grid pattern comprises a forming a diamond shaped grid pattern.

14. The method of claim 12 wherein forming a locally thin layered substrate comprises juxtaposing two sheets of material with parallel lines that are regularly spaced and form a diamond pattern.

15. The method of claim 12 further comprising placing the at least one material reference object in air spaces of the grid pattern along the length of the device and running down the length of the curved scanner table top at the center and along at least one side.

16. The method of claim 12 wherein measuring resolution, noise, and signal response properties comprises measuring image quality of CT, XR, PET/CT, NM, MRI, or Ultrasound scans.

17. A CT disk phantom comprising: an inner cylinder of air material surrounded by a second cylinder of a high density material; a third cylinder of a different third material concentrically surrounding the inner cylinder and second cylinder; and a fourth cylinder of a different fourth material concentrically surrounds the inner cylinder, the second cylinder and the third cylinder.

18. The phantom of claim 17 further comprising a casing enveloping the second through fourth cylinders with an opening leaving the inner surface of the second cylinder surrounding the inner cylinder and the inner cylinder uncovered.

19. The phantom of claim 18 wherein the casing comprises urethane.

20. The phantom of claims 17 or 18 wherein the second through optional fourth cylinder materials are selected from the group consisting of Polytetrafluoroethylene (PTFE), Polyoxymethylene (POM), low-density polyethylene (LDPE) plastic and combinations thereof.

21. The phantom of claim 17 further comprising: a radial pattern affixedly centered on a top face of the CT disk; and a clock is coupled to uniformly rotate the top face to rotate the pattern.

22. A method for measuring the temporal resolution of a scanner comprising: coupling a clock is to rotate the top face with the radial pattern; scanning the rotating radial pattern for a predetermined time period to produce a resulting rotation pattern; and measuring the rotation pattern to determine the temporal resolution of the scanner.

\* \* \* \* \*